United States Patent [19]

Peters

[11] Patent Number: 5,411,549
[45] Date of Patent: May 2, 1995

[54] SELECTIVELY EXPANDABLE, RETRACTABLE AND REMOVABLE STENT

[75] Inventor: Jeffrey J. Peters, Golden Valley, Minn.

[73] Assignee: Scimed Life Systems, Inc., Maple Grove, Minn.

[21] Appl. No.: 91,162

[22] Filed: Jul. 13, 1993

[51] Int. Cl.⁶ .............................................. A61F 2/06
[52] U.S. Cl. ......................................... 623/1; 623/11; 623/12; 606/194; 606/195
[58] Field of Search ............... 623/1, 11, 12; 606/151, 606/153, 155, 156, 191, 192, 194, 195, 198

[56] References Cited

U.S. PATENT DOCUMENTS

| Re. 34,327 | 7/1993 | Kreamer | 623/1 |
|---|---|---|---|
| 4,183,102 | 1/1980 | Guiset | 3/1.4 |
| 4,693,249 | 9/1987 | Schenck et al. | 128/334 |
| 4,733,665 | 3/1988 | Palmaz | 128/343 |
| 4,740,207 | 4/1988 | Kreamer | 623/1 |
| 4,877,030 | 10/1989 | Beck et al. | 128/343 |
| 5,007,926 | 4/1991 | Derbyshire | 623/1 |
| 5,266,073 | 11/1993 | Wall | 623/1 |

FOREIGN PATENT DOCUMENTS

0554082A1  4/1993  European Pat. Off. ........ A61F 2/06

Primary Examiner—Randy C. Shay
Attorney, Agent, or Firm—Vidas, Arrett & Steinkraus

[57] ABSTRACT

An improved stent apparatus for intraluminal use in the body of an animal. The apparatus is of resilient material disposed in a tubular configuration about a central axis, which carries ratchet apparatus in the form of catch and latch apparatus having a selectively removable latch. The stent is expanded through the use of an angioplasty balloon to any selected one of a plurality of dilated positions. As the stent expands, the catches come into contact with the latch to prevent retraction of the stent apparatus. The latch communicates with a point external to the lumen, and is selectively removable from contact with the catches to enable the stent apparatus to return to its original diameter.

18 Claims, 3 Drawing Sheets

SELECTIVELY EXPANDABLE, RETRACTABLE AND REMOVABLE STENT

BACKGROUND OF THE INVENTION

1. Field of the Invention

The present invention relates generally to medical devices, and more particularly to medical devices intended for use within the body of an animal, and still more particularly to a stent and/or perfusion apparatus for selective intraluminal insertion and expansion. The apparatus of this invention provides an intraluminal stent that is, when used with a proper expansion device, selectively expandable, retractable and removable.

2. Description of the Prior Art

The use of stents as intraluminal expansion and perfusion apparatus is known to those of skill in the art. Many such devices are known as are the materials and methods for making them, and various apparatus useful in the placement of the stent in the lumen or vessel when desired.

U.S. Pat. No. 4,733,665, issued Mar. 29, 1988 to J. C. Palmaz describes an expandable stent for placement in the blood vessel of an animal. The Palmaz teaching is for a wire mesh stent that is expandable through use of an angioplasty balloon. The stent is to be used as a permanent graft.

U.S. Pat. No. 5,007,926 issued Apr. 16, 1991 to G. Derbyshire describes another stent adapted to be expanded by a balloon catheter. This stent includes ratchet means for allowing the selection of an expanded diameter for the stent. Derbyshire teaches that this stent is removable, but to do so the stent must be redilated to release the ratchet catch, and then a forceps is applied to remove the device.

U.S. Pat. No. 4,740,207, issued Apr. 26, 1988 to J. W. Kreamer also teaches a stent device selectively expandable by a balloon catheter which includes a retaining ledge on its inside wall that catches the edge of the expanding stent to hold it in a dilated position. There is no teaching in Kreamer of a means for retraction of the device once it has been dilated to a catch position.

U.S. Pat. Nos. 4,183,102, 4,693,249 and 4,877,030 all teach stent devices that are selectively expandable within a duct or vessel and which have some form of catch to hold in the expanded position. These devices are limited to a single catch expansion position and there are no means taught for the selective and simple removal of the stents.

SUMMARY OF THE INVENTION

The present invention overcomes the disadvantages found in the prior art by providing stent apparatus that can be selectively expanded to a plurality of dilated diameters within the lumen of a body, and retracted back to its original diameter and removed from the lumen with comparative ease.

BRIEF DESCRIPTION OF THE DRAWINGS

Other objects and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
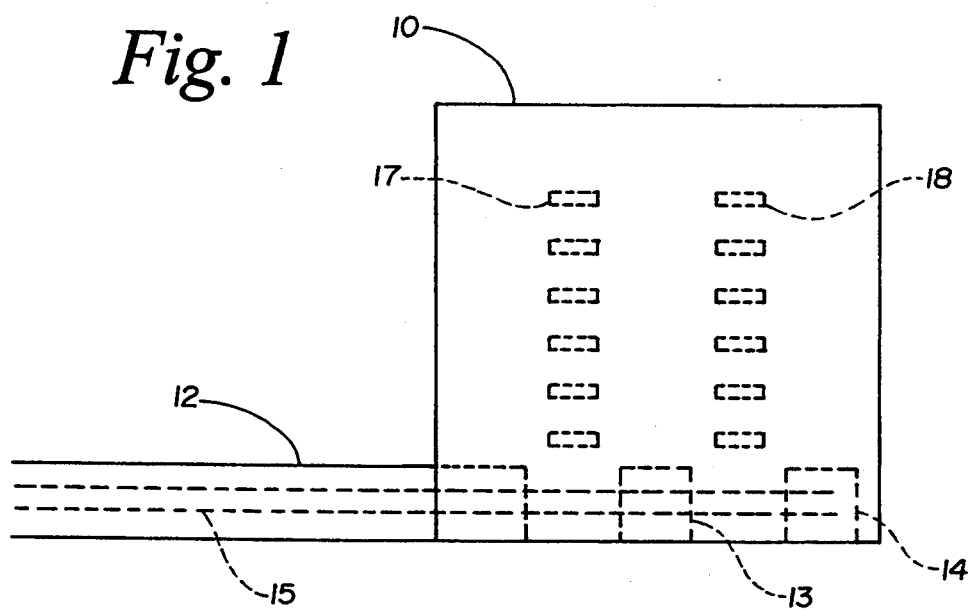
FIG. 1 is a plan view showing a first preferred embodiment of the stent of this invention including the ratchet or catch means and the means for placing or removing the stent device.

Referring first to FIG. 1 there is shown a stent formed by a generally rectangular member 10. Member 10 is preferably made of a resilient, thermoplastic or thermoset material, substantially inert to body fluids and tissue. Also shown are two columns of flexible tabs or catches 17 and 18 which form a detent device for coacting with a latch device 15. Preferably, the two columns of tabs 17 and 18 are formed by cutting or punching them out of member 10. Latch 15, in the preferred embodiment, is a length of stainless steel wire slidably mounted in a latch holding device, here shown as three sections of tubing 12, 13 and 14, secured to member 10. Section 12 is preferably of sufficient length to extend out of the body after the stent apparatus has been placed in any selected lumen. Thus, when the stent has been used as desired and retracted to its original diameter, in a manner described below, it can be removed from the lumen or vessel by pulling on tube section 12. One acceptable length of section 12 for this preferred embodiment has been found to be approximately 140 centimeters. Preferably, latch 15 is sufficiently longer than tube section 12 so that it extends therefrom thus facilitating the movement of latch 15 alone, when it is desired to leave the stent in place for a further length of time.

Figure 2:
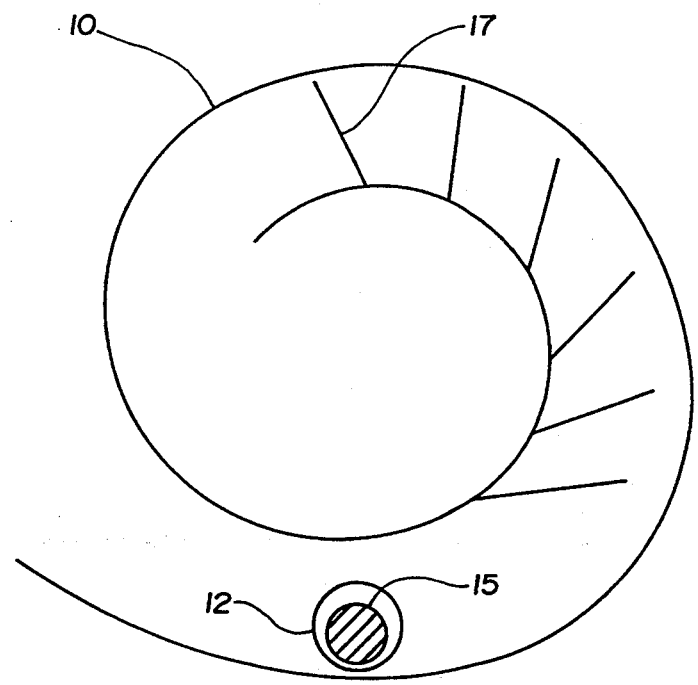
FIG. 2 is a side plan view of the apparatus of FIG. 1 showing the stent apparatus of this invention in its initial or retracted position.

Referring now to FIG. 2, member 10 is shown in its fully retracted or minimum diameter form. It can be seen that member 10 forms a generally tubular shape that is coiled about an imaginary inner transverse axis. Tubular section 12 is shown mounted on an inner wall of member 10, and latch wire 15 is shown in place within tube 12. It can also be seen that the column of flexible tabs 17 that sit on an outer wall of member 10 are carried by the coiling of member 10 to a point where none of the tabs 17 are in contact with latch wire 15. In operation, another device such as an angioplasty balloon catheter (not shown) is placed within the lumen formed by member 10 along its transverse axis, and as the balloon is inflated the resulting pressure on the inner wall of the stent formed by member 10 will cause stent 10 to uncoil.

Figure 3:
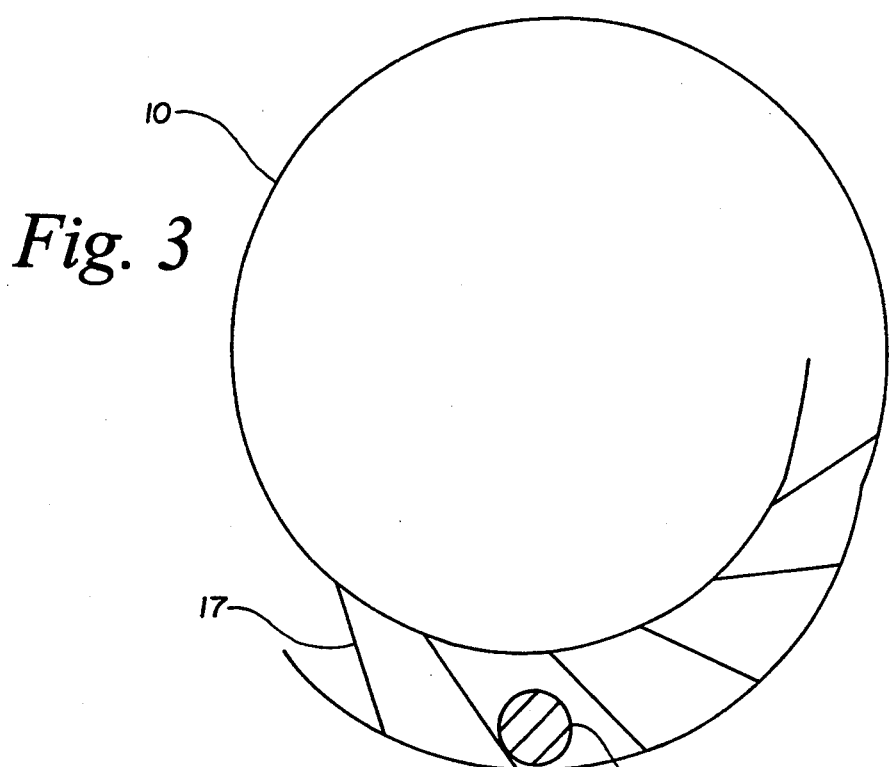
FIG. 3 is a view the same as FIG. 2 showing the apparatus of this invention in one of its expanded positions.

Referring now to FIG. 3, member 10 is shown in one of its expanded or dilated positions. As is clear from the view of FIG. 3, one of the flexible tabs or catches of column 17 has been moved into contact with latch wire 15. A corresponding tab or catch of column 18 (not seen) will also be in contact with latch 15. (The outline of tube sections 12, 13 and 14 have been removed from FIG. 3 for purposes of clarity.) In this position, for example, the balloon catheter could be removed from the lumen of stent 10 but the resilient member 10 would retain this expanded position due to the contact of the catches of columns 17 and 18 with latch wire 15.

Referring again to FIG. 1 in conjunction with FIG. 3, it can be seen that the catch of column 17 contacts wire 15 at the spaced interval between tube sections 12 and 13, while the catch of column 18 contacts wire 15 at the space between tube sections 13 and 14. It will also be apparent from the above described drawings that a selection of six expanded or dilated positions or diameters of member 10 are available, directly related to the number of tabs or catches in each of columns 17 and 18. It is within the scope of this invention to provide only a single column of catches, or even only one catch, in which case just two tube sections of tube would be mounted on the inner wall of member 10 in spaced relation, to form the latch mount device for wire 15.

With reference again to FIGS. 1–3, it will be apparent that when the stent of member 10 of this invention is in place within a lumen or vessel, and it has been expanded to one of its dilated positions and the balloon catheter has been removed, the stent will remain in its expanded position to apply force to the walls of the lumen or vessel to hold it open for any desired medical purpose, such as relief of spasm, dissection or arterial passive perfusion. Member 10 can be placed into the lumen or vessel by being carried by another device such as a balloon catheter, or can be placed in a lumen through the use of pressure on elongated tube section 12. Wire 15 can be slide into place within section 12 to add rigidity during placement of the stent of this invention, or can be removed during placement to add flexibility to the device.

As shown in FIGS. 1–3, when desired, latch 15 can be fully or partially retracted to take it out of contact with the catches of columns 17 and 18, and the resilience of member 10 will then cause it to return to its original, heat set coiled position, giving the stent a minimum diameter to facilitate removal of the stent from the lumen or vessel. Or, if desired, the retracted member 10 can selectively be moved to another point within the lumen or vessel, the latch wire 15 can be returned to its mount formed by tube sections 12–14, and the stent can be selectively expanded once again to any of the six available dilated positions.

Figure 4A:
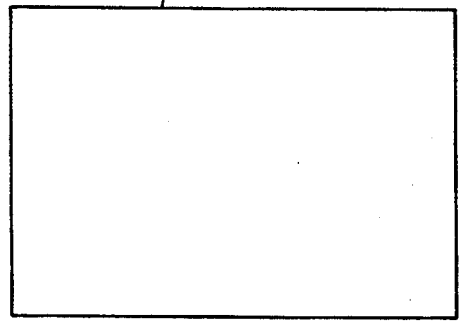
FIGS. 4a-4c are top plan views showing the construction stages of the stent apparatus of this invention.
Figure 4B:
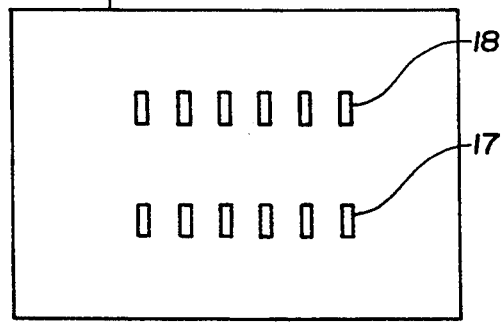
Figure 4C:
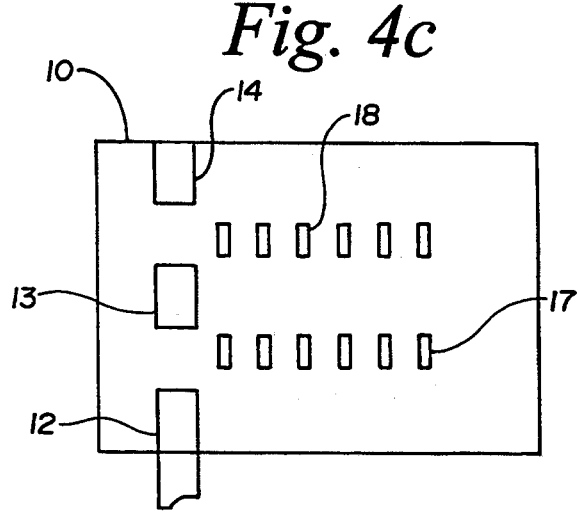

Referring now to FIGS. 4a, 4b and 4c, a preferred method for manufacturing the stent of this invention is revealed. In FIG. 4a there is shown generally rectangular member 10 preferably of a heat settable or curable thermoplastic or thermoset or other resilient biocompatible material. In this preferred embodiment, a pair of columns 17 and 18 of six tabs each are cut or punched from the material of member 10. As seen in FIG. 4b, the tabs of columns 17 and 18 are cut to cause slots in member 10, and in this view the flexible tabs extend away from the viewer. FIG. 4c discloses the next step in construction of the stent of this invention, which is the placement of a latch mounting device in the form of tube sections 12, 13 and 14. Tube sections 12–14 are mounted, for example by bonding, on a side of member 10 opposite to the direction in which the tabs of columns 17 and 18 extend, and in spaced relation such that each of the spaces between sections 12 and 13, and 13 and 14 align, respectively, with columns 17 and 18. Tube section 12 is preferably of sufficient length so as to extend out of the lumen, duct or vessel and thence out of the body into which the member 10 is to be placed. It has been found that a length of about 140 cm. for tube section 12 will provide the desired extension beyond the body after insertion of the stent. When the tube sections 12–14 have been mounted on member 10, and the two columns 17 and 18 of six tabs each have been formed from member 10, the entire apparatus shown in FIG. 4c is heat set to cause it to take the form of a generally tubular coil about a transverse axis as shown in FIG. 2.

Figure 5:
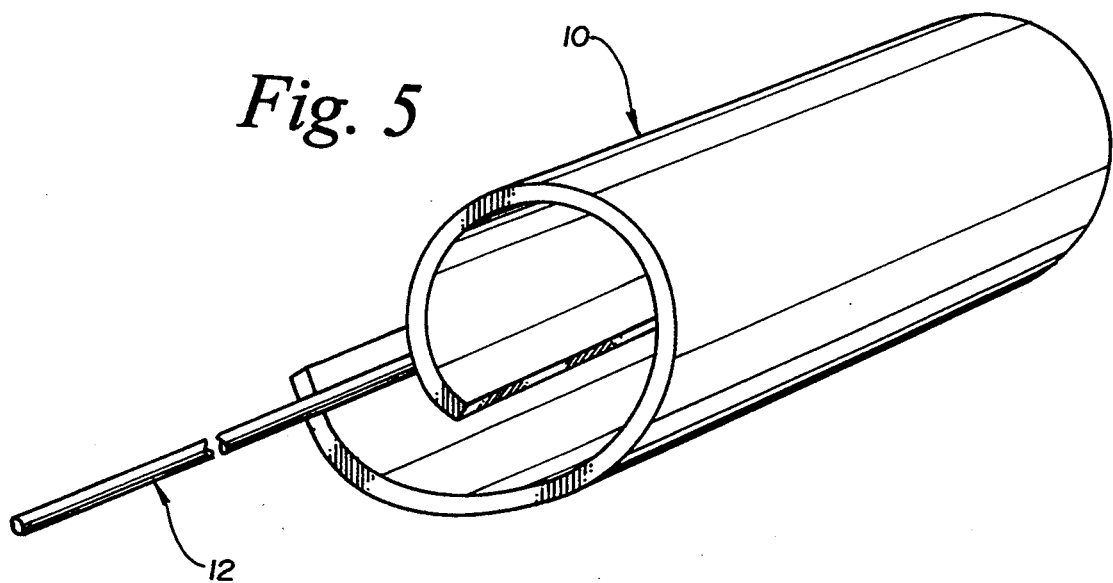
FIG. 5 is a perspective view of the apparatus of this invention.

Reference is now made to FIG. 5 which shows in perspective the apparatus described above following the heat setting process, and shown in the plan views of FIGS. 2 and 4c. Here it can be seen how tube 12 extends from the coil-like shape of member 10.

As described above, a latch wire 15 (not shown in FIG. 5) of a corrosion resistant material such as stainless steel, may then be passed through tube sections 12–14 to act as a latch in conjunction with the flexible tabs or catches of columns 17 and 18.

Figure 6:
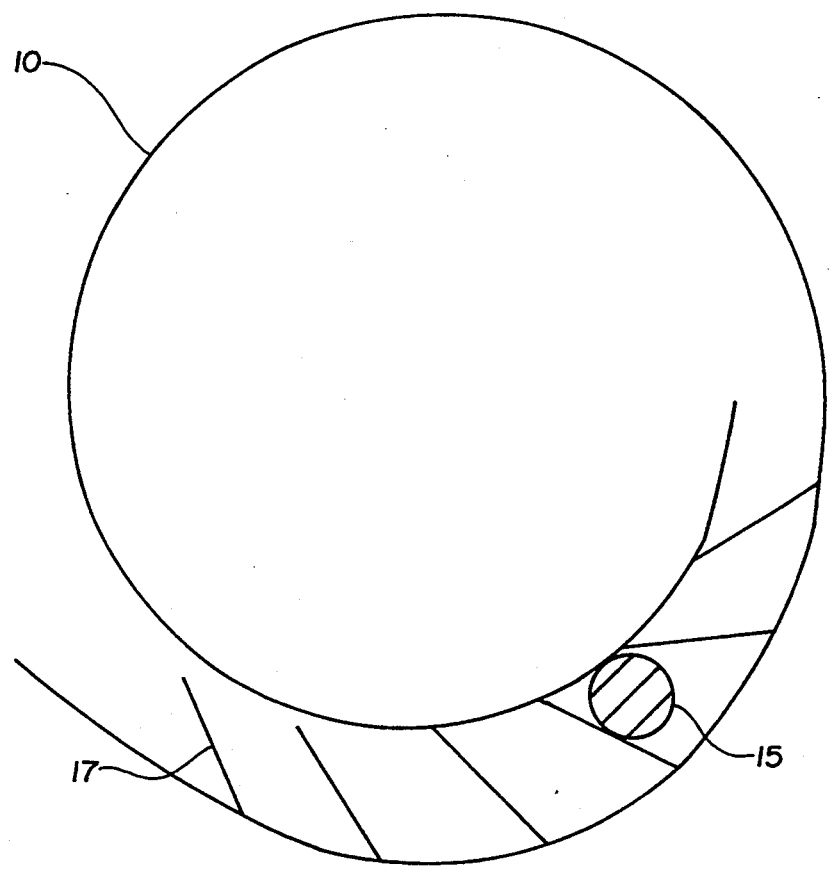
FIG. 6 is a view similar to FIGS. 2 and 3 but concerns a second preferred embodiment of the apparatus of this invention.

Referring now to FIG. 6, there is shown a plan view of a second preferred embodiment of the apparatus of this invention. In this second embodiment, latch wire 15 and tabs or catches 17 are each on opposite sides of member 10 than in the above described embodiment. Thus latch 15 is shown on the outside of member 10, while catches 17 are on the inside. (Mounting means for latch 10 are provided as in the above described embodiment, but are not shown in FIG. 6 for purposes of clarity.) The effective result is that as member 10 expands or uncoils, latch wire 15 will be carried to tabs 17, rather than vice-versa. In all other respects the embodiment of FIG. 6 works in the same manner as the embodiment of FIGS. 1–5.

The primary advantages of this second embodiment are: it enables the use of a smaller profile for the stent apparatus of this invention; and, there is little chance of tabs 17 causing a trauma in the walls of the lumen where the stent is placed, because tabs 17 will remain within the coil formed by member 10.

Having thus described the preferred embodiments of the present invention, those of skill in the art will readily appreciate the other useful embodiments within the scope of the claims hereto attached.

I claim:

1. Stent apparatus comprising:
   a. a resilient member disposed in a generally tubular, coiled manner about a transverse axis, having a minimum diameter when in a relaxed coiled position and being selectively expandable to one or more increasingly greater diameters;
   b. said member having a first side and a second side; and,
   c. movable latch device on said first side that is movable relates to the resilient member and a detent device on said second side, such that expansion of said resilient member from said relaxed coiled position causes said detent device and said movable latch device to make contact to hold said member in an expanded position, and movement of said latch device causes release of the detent device.

2. The apparatus of claim 1 including a latch mounting device for removably mounting said movable latch device on said first side such that removal of said movable latch device causes said resilient member to retract to said relaxed coiled position.

3. The apparatus of claim 2 in which said detent device comprises at least one row of two or more catches aligned parallel to said transverse axis.

4. The apparatus of claim 3 including a plurality of said rows of two or more catches, each of said rows being parallel to said transverse axis and to one another and said catches being aligned to form parallel columns to said second side.

5. The apparatus of claim 4 in which said latch mounting device comprises a plurality of tubular members mounted on said first side in spaced relation and along a central axis parallel to said transverse axis, and said movable latch device comprises a latch bar slidably mounted in said tubular members.

6. The apparatus of claim 2, 3, or 4 including a retraction device connected to said resilient member for moving and removing said member after it has been placed in a body, said retraction device comprising an elongated tubular element for extending from a body after said member has been placed in the body, and said tubular element comprising at least a portion of said latch mounting device.

7. The apparatus of claim 2 in which said latch mounting device comprises a plurality of tubular members mounted on said first side in spaced relation and along a central axis parallel to said transverse axis, and said movable latch device comprises a latch bar slidably mounted in said tubular members.

8. The apparatus of claim 3 in which said latch mounting device comprises a plurality of tubular members mounted on said first side in spaced relation and along a central axis parallel to said transverse axis, and said movable latch device comprises a latch bar slidably mounted in said tubular members.

9. The apparatus of claim 1 in which said detent device comprises at least one row of two or more catches aligned parallel to said transverse axis.

10. The apparatus of claim 9 including a plurality of said rows of two or more catches, each of said rows being parallel to said transverse axis and to one another and said catches being aligned to form parallel columns on said second side.

11. The apparatus of claim 10 including a latch mounting device for removably mounting said movable latch device on said first side such that removal of said movable latch device causes said resilient member to retract to said relaxed coiled position, wherein said latch mounting device comprises a plurality of tubular members mounted on said first side in spaced relation and along a central axis parallel to said transverse axis, and said movable latch device comprises a latch bar slidably mounted in said tubular members.

12. The apparatus of claim 1, 2, 9, 3, 11 or 4 including a retraction device connected to said resilient member for moving and removing said member after it has been placed in a body.

13. The apparatus of claim 1, 2, 9, 3, 11 or 4 including a retraction device connected to said resilient member for moving and removing said member after it has been placed in a body, said retraction device comprising an elongated element for extending from a body after said member has been placed in the body.

14. The apparatus in claim 9 including a latch mounting device for removably mounting said movable latch device on said first side such that removal of said movable latch device causes said resilient member to retract to said relaxed coiled position, wherein said latch mounting device comprises a plurality of tubular members mounted on said first side in spaced relation and along a central axis parallel to said transverse axis, and said movable latch device comprises a latch bar slidably mounted in said tubular member.

15. The apparatus of claim 7, 14, 8, 11 or 5 in which said space or spaces between said tubular members align with a respective column or columns formed by said catches.

16. The apparatus of claim 7, 14, 8, 11 or 5 in which said stent apparatus comprises an interluminal stent, at least one of said tubular members extends beyond said first side of said resilient member to a point which is intended to be external to a lumen when the resilient member is disposed within the lumen, and said latch bar is slidably mounted within and through said extended tubular member.

17. The apparatus of claim 9, 3, 10, 4, 14, 8, 11 or 5 in which each of said catches is formed from the body of said resilient member.

18. The apparatus of claim 7, 8, 9, 10 or 11 including a retraction device connected to said resilient member for moving and removing said member after it has been placed in a body, said retraction device comprising an elongated tubular element for extending from a body after said member has been placed in the body, and said tubular element comprising one of said plurality of tubular members of said latch mounting device.

* * * * *